United States Patent
Mamedov et al.

(10) Patent No.: US 9,249,079 B2
(45) Date of Patent: Feb. 2, 2016

(54) PROCESS FOR INCREASING THE CARBON MONOXIDE CONTENT OF A SYNGAS MIXTURE

(71) Applicant: SAUDI BASIC INDUSTRIES CORPORATION, Riyadh (SA)

(72) Inventors: Aggadin Kh. Mamedov, Sugar Land, TX (US); Mubarak Bashir, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/546,539

(22) Filed: Nov. 18, 2014

(65) Prior Publication Data

US 2015/0080482 A1   Mar. 19, 2015

Related U.S. Application Data

(62) Division of application No. 13/140,405, filed as application No. PCT/EP2009/008980 on Dec. 15, 2009, now Pat. No. 8,946,308.

(30) Foreign Application Priority Data

Dec. 17, 2008   (EP) ..................... 08075947

(51) Int. Cl.

| | | |
|---|---|---|
| C07C 1/04 | (2006.01) | |
| C07C 41/01 | (2006.01) | |
| C01B 3/34 | (2006.01) | |
| C07C 29/151 | (2006.01) | |
| C10G 2/00 | (2006.01) | |
| C10K 3/02 | (2006.01) | |
| C07C 29/136 | (2006.01) | |
| B01J 23/26 | (2006.01) | |

(52) U.S. Cl.
CPC . *C07C 41/01* (2013.01); *C01B 3/34* (2013.01); *C07C 29/136* (2013.01); *C07C 29/1518* (2013.01); *C10G 2/32* (2013.01); *C10K 3/02* (2013.01); *B01J 23/26* (2013.01); *C01B 2203/025* (2013.01); *C01B 2203/0233* (2013.01); *C01B 2203/0238* (2013.01); *C01B 2203/0244* (2013.01); *C01B 2203/047* (2013.01); *C01B 2203/0435* (2013.01); *C01B 2203/0495* (2013.01); *C01B 2203/06* (2013.01)

(58) Field of Classification Search
CPC .............. C07C 1/04; C10G 2/00; C10G 2/32; C10G 2/33
USPC .......................................................... 518/706
See application file for complete search history.

(56) References Cited

U.S. PATENT DOCUMENTS

| | | | |
|---|---|---|---|
| 3,718,418 A * | 2/1973 | Fleming et al. ............. | 423/418.2 |
| 4,265,868 A | 5/1981 | Kamody | |
| 4,654,458 A | 3/1987 | Jezl et al. | |
| 4,714,657 A | 12/1987 | Quinn et al. | |
| 5,068,057 A | 11/1991 | Gustafson et al. | |
| 5,714,657 A | 2/1998 | DeVries | |
| 5,911,964 A | 6/1999 | Iwanami et al. | |
| 6,043,288 A | 3/2000 | DeGeorge et al. | |
| 2003/0113244 A1 | 6/2003 | Dupont et al. | |
| 2004/0191164 A1 | 9/2004 | Schiodt et al. | |
| 2005/0043417 A1 | 2/2005 | O'Rear | |
| 2005/0232833 A1 | 10/2005 | Hardy et al. | |
| 2007/0129450 A1 | 6/2007 | Barnicki et al. | |
| 2007/0142482 A1* | 6/2007 | Jung et al. ..................... | 518/726 |
| 2008/0021121 A1 | 1/2008 | Norbeck et al. | |
| 2008/0031809 A1 | 2/2008 | Norbeck et al. | |

FOREIGN PATENT DOCUMENTS

| | | |
|---|---|---|
| CN | 1270157 A | 10/2000 |
| CN | 1416404 A | 5/2003 |
| CN | 1523082 A | 8/2004 |
| EP | 0291857 A2 | 11/1988 |
| EP | 0898136 A2 | 2/1999 |
| EP | 1153660 A2 | 11/2001 |
| GB | 2168718 A | 6/1986 |
| JP | H08245211 A | 9/1996 |
| JP | H09100108 A | 4/1997 |
| JP | 2000219508 A | 8/2000 |
| JP | 2000233917 A | 8/2000 |
| JP | 2000233918 A | 8/2000 |
| JP | 2003525832 A | 9/2003 |
| JP | 2004238282 A | 8/2004 |

(Continued)

OTHER PUBLICATIONS

Chinese Patent No. 1270157 (A); Publication Date: Oct. 18, 2000; Abstract Only; 2 Pages.

(Continued)

*Primary Examiner* — Sudhakar Katakam

(74) *Attorney, Agent, or Firm* — Cantor Colburn LLP

(57) ABSTRACT

The invention relates to a process for increasing the carbon monoxide content of a feed gas mixture comprising carbon dioxide, hydrogen and carbon monoxide via a catalytic reversed water gas shift reaction, comprising the steps of (1) heating the feed gas mixture having an initial feed temperature of at most 350° C. in a first zone to a temperature within a reaction temperature range in the presence of a first catalyst; and (2) contacting the heated feed gas in a second zone within the reaction temperature range with a second catalyst. This process shows relatively high conversion of carbon dioxide, and virtually no methane or coke is being formed, allowing stable operation.

11 Claims, No Drawings

(56) References Cited

FOREIGN PATENT DOCUMENTS

| JP | 2008525448 A | 7/2008 |
|---|---|---|
| JP | 2010531221 A | 9/2010 |
| WO | 9524367 A1 | 9/1995 |
| WO | 9709293 A1 | 3/1997 |
| WO | 0166463 A1 | 9/2001 |
| WO | 2008131898 A1 | 11/2008 |
| WO | 2009000494 A2 | 12/2008 |

OTHER PUBLICATIONS

Chinese Search Report; Chinese Application No. 200980150470.3; Mailing Date: Apr. 7, 2013; 8 Pages.
Deng et al.; "Oxidative Dehydrogenation of Ethane with Carbon Dioxide to Ethylene Over Nanosized Cr2O3 Catalysts"; Chinese Journal of Catalysis; vol. 24, No. 10; Oct. 2003; Abstract Only; 19 Pages.
Extended European Search Report; European Application No. 08075947.5; Mailing Date: Jun. 3, 2009; 5 Pages.
Hisanori Ando et al., "Methanation of Carbon Dioxide Over LaNi4X Type Catalysts" Energy Convers. Mgmt. vol. 36, No. 6-9, pp. 653-656, 1995; 4 pages.
International Preliminary Report on Patentability; International Application No. PCT/EP2009/008980; International Filing Date: Dec. 15, 2009; Mailing Date: Jun. 30, 2011; 6 Pages.
International Search Report; International Application No. PCT/EP2009/008980; International Filing Date: Dec. 15, 2009; Mailing Date: Mar. 26, 2010; 7 Pages.
Japanese Patent No. 2000219508 (A); Publication Date: Aug. 8, 2000; Machine Translation; 11 Pages.
Japanese Patent No. 2000233917 (A); Publication Date: Aug. 29, 2000; Machine Translation; 9 Pages.
Japanese Patent No. 2000233918 (A); Publication Date: Aug. 29, 2000; Machine Translation; 14 Pages.
Japanese Patent No. H08245211 (A); Publication Date: Sep. 24, 1996; Machine Translation; 10 Pages.
Japanese Patent No. H09100108 (A); Publication Date: Apr. 15, 1997; Machine Translation; 5 Pages.
Ohno et al.; "Slurry Phase DME Direct Synthesis Technology: 100 Tons/Day Demonstration Plant Operation and Scale Up Study"; Natural Gas Conversion Symposium; 2007; 12 Pages.
S. Sugawa et al., "Methanol Synthesis from CO2 and H2 Over Silver Catalyst" Energy Convers. Mgmt vol. 36, No. 6-9, pp. 665-668, 1995; 4 pages.
Written Opinion of the International Searching Authority; International Application No. PCT/EP2009/008980; International Filing Date: Dec. 15, 2009; Mailing Date: Mar. 26, 2010; 5 Pages.
Y. Kanai et al., "Role of ZnO in Promoting Methanol Synthesis Over a Physically-Mixed Cu/SiO2 and ZnO/SiO2 Catalyst" Energy Convers. Mgmt vol. 36, No. 6-9, pp. 649,652, 1995; 4 pages.
Japanese Patent No. 2008525448; Date of Publication: Jul. 17, 2008; Abstract Only, 1 page.

* cited by examiner

PROCESS FOR INCREASING THE CARBON MONOXIDE CONTENT OF A SYNGAS MIXTURE

CROSS REFERENCE TO RELATED APPLICATIONS

The present application is a divisional of U.S. application Ser. No. 13/140,405, filed Aug. 29, 2011, which is a 371 filing of International Application No. PCT/EP2009/008980, filed Dec. 15, 2009, which claims priority to European Application No. 08075947.5, filed Dec. 17, 2008, all of which are hereby incorporated by reference in their entirety.

TECHNICAL FIELD

The invention relates to a process for increasing the carbon monoxide (CO) content of a feed gas mixture comprising carbon dioxide ($CO_2$), hydrogen ($H_2$) and CO via a catalytic reversed water gas shift reaction (RWGS).

BACKGROUND

Such a process is for example known from the patent application JP2000-233918A. This document describes a process wherein a hydrocarbon is first reformed into a syngas (generally used abbreviation for synthesis gas) mixture comprising CO, $CO_2$, and $H_2$ and optionally other components like water, hydrocarbons like methane, and nitrogen. The syngas is cooled, condensed water is separated, and then CO is separated with a pressure swing adsorption process (PSA). An off-gas stream comprising mainly $CO_2$, $H_2$ and some CO is heated to 740° C. in a heater, and then introduced into a RWGS reactor packed with a RWGS catalyst having Fe and Cr as its main components, to react part of the $CO_2$ into CO.

The reverse water gas shift reaction, or the backward reaction generally referred to as water gas shift reaction, is an equilibrium reaction that can be represented as:

$$CO_2 + H_2 \leftrightarrows CO + H_2O$$

Conversion of $CO_2$ to CO by a catalytic RWGS reaction is recognized as a promising process for $CO_2$ utilization, and has been subject of numerous publications. The equilibrium constant of the RWGS reaction would be about 1 at 800° C., meaning higher temperatures are needed to shift the equilibrium and favour CO being formed. Various catalysts have been proposed to enable lower reaction temperatures. Also depending on the catalyst applied, some methane may be formed as by-product as a result of methanation reactions:

$$CO + 3H_2 \leftrightarrows CH_4 + H_2O$$

$$CO_2 + 4H_2 \leftrightarrows CH_4 + 2H_2O$$

In U.S. Pat. No. 5,714,657 a multistep process is described for converting natural gas into higher hydrocarbons via syngas, wherein the obtained gas mixture of CO and $H_2$ is reacted with $CO_2$ at a temperature of 800-1300° C. in the absence of a catalyst, to increase the amount of CO that is subsequently further reacted with water in a so-called Koelbel-Engelhard reaction. Process efficiency is increased by separating the by-product $CO_2$ and using it in the thermal RWGS reaction.

A process wherein a hydrocarbon is reformed to give a syngas mixture, to which carbon dioxide is added and then contacted with a RWGS catalyst, is known from GB2168718A; but this publication provides no further details on reaction conditions or catalysts to be applied.

US2004/191164 relates to a process for the treatment of syngas to increase the content of $H_2$ and/or CO by the reverse water gas shift reaction comprising the step of contacting the syngas with a manganese- and zirconium-oxide comprising catalyst. US2004/191164 describes that the inlet temperature of the zone in which the catalyst is confined must be between 500 and 1000° C. and that the used reactor allows for the feedgas to be heated to the desired temperature before reaching the catalyst.

US2003/113244 relates to a process for producing CO by reverse water gas shift reaction in the presence of zinc- and chromium-oxide catalyst, wherein the reaction is carried out at a temperature of 300-500° C. In the processes described in US2003/113244, the syngas mixture is heated to temperatures in the range of 300-520° C. before it is reacted by passing over a catalyst bed.

U.S. Pat. No. 5,911,964 relates to a method for reducing $CO_2$ by catalytic reversed water gas shift reaction, which is characterized in that the catalyst comprises a transition metal on a zinc oxide-comprising carrier. The reaction is preferably conducted at a temperature of about 400-600° C. or more. U.S. Pat. No. 5,911,964 is silent on the temperature of the feed gas mixture before contacting it with the catalyst at reaction temperature.

U.S. Pat. No. 3,718,418 discloses a process wherein the reversed water gas shift reaction is carried out in the presence of Rh and Ru metals and alloys thereof with Pt as a catalyst. The process according to U.S. Pat. No. 3,718,418 is carried out by passing the feed gas into contact with the catalyst in a reactor chamber and heating said chamber within the range of 175-500° C. Preferably, the reactor chamber is maintained at a temperature of about 175-275° C.

US2007/0142482A1 discloses a method for producing dimethyl ether (DME) directly from syngas, wherein a $CO_2$-rich stream is separated from a crude DME product stream and reacted with hydrogen in the presence of a RWGS catalyst at a temperature of 500-1000° C. to form a CO-rich stream, which is fed to the DME forming step. The amount of CO present in the $CO_2$-rich stream is very low, e.g. well below 1 vol %.

A disadvantage of the known process for increasing the CO content of a feed gas mixture comprising $CO_2$, $H_2$ and CO via the RWGS reaction is that coke is being formed and deposited on e.g. reactor wall, gas-distribution plates or particles, and catalyst particles; leading to clogging of the reactor and/or catalyst deactivation.

Coke formation can be the result of various reactions; like thermal cracking of methane, or decomposition of carbon monoxide via the so-called Boudouard reaction:

$$CO \leftrightarrows C + CO_2$$

The Boudouard reaction is especially likely to occur in gas mixtures having a relatively high CO content.

It is therefore an objective of the present invention to provide a process for increasing the CO content of a feed gas mixture comprising $CO_2$, $H_2$ and CO via the RWGS reaction wherein no or very little coke formation occurs.

SUMMARY

This object is achieved according to the invention with such a process that comprises the steps of (1) heating the feed gas mixture having an initial feed temperature of at most 350° C. in a first zone to a temperature within a reaction temperature range in the presence of a first catalyst;

(2) contacting the heated feed gas in a second zone within the reaction temperature range with a second catalyst.

DETAILED DESCRIPTION

In the context of the present invention, the term "heating the feed gas mixture in the presence of a catalyst" is meant to describe that while heating the feed gas mixture, the catalyst must be close enough to the feed gas mixture to exhibit its catalytic activity.

Accordingly, the process of the present invention is characterized in that the feed gas mixture is in contact with a catalyst when said feed gas is having a temperature of more than 350° C. For instance, the feed gas mixture may not be heated to a temperature of more than 350° C. while being present in a heat exchanger where no catalyst is present or in a section of a reactor where no catalyst is present, like a top part of a vertical reactor not completely filled with a catalyst bed.

Hence, the step of "heating the feed gas mixture having an initial feed temperature of at most 350° C. in a first zone to a temperature within a reaction temperature range in the presence of a first catalyst" describes "contacting a feed gas mixture having an initial feed temperature of at most 350° C. in a first zone with a first catalyst and heating said feed gas mixture to a temperature within a reaction temperature range in contact with said first catalyst".

With the process according to the invention the CO content of a gas mixture comprising $CO_2$, $H_2$ and CO can be increased without significant amounts of coke being formed, which could otherwise deposit on for example reactor parts and/or catalyst particles. The process according to the invention shows relatively high conversion of carbon dioxide, virtually no methane in its product stream, and stable operation.

It is a surprising advantage of the process according to the invention that good $CO_2$ conversion into CO can be obtained also with the feed gas comprising relatively high amounts of CO; as the skilled person is aware of above-mentioned potential coke formation as known from prior art, but also of the RWGS equilibrium being forced in the other direction by increased CO levels.

The process according to the invention can be operated in known reactors, and be easily combined or even integrated with other process steps; such as hydrocarbon reforming steps, or subsequent reactions of the modified syngas into other chemicals like methanol, DME, or other hydrocarbons.

The process according to the invention is particularly advantageous in combination with making chemicals from syngas that require a syngas composition with relatively low $H_2$ to CO ratio, or even about equimolar amounts, like the direct conversion of syngas into DME, which can be represented by the overall reaction scheme:

In the process according to the invention a feed gas mixture comprising $CO_2$, $H_2$ and CO is used. This feed gas can be obtained from any source. The feed gas can be made by mixing several gasses or mixed gas streams, be obtained from a reforming reaction on a hydrocarbon feedstock like natural gas or naphtha, or by a combination of methods. Suitable reforming processes include steam reforming, partial oxidation, dry reforming, and combinations thereof like autothermal steam reforming or autothermal dry reforming. The choice of reforming reaction, and thus of the feed gas composition, will also be dependent on the targeted use of the gas mixture obtained with the process of the invention. The feed gas may further comprise other gasses, provided that these do not negatively influence the reaction, such as steam or an inert gas like nitrogen. Steam concentration is generally low, as reformer effluent—syngas—is typically quenched to condense and separate water (and to prevent the Bououard reaction). The feed gas preferably does not contain alkanes or other hydrocarbons, as they will induce coke formation at the elevated temperatures applied in the process.

It is a specific advantage of the process according to the invention that a feed gas containing CO can be reacted without coke formation. The CO content of the feed gas is therefore preferably at least 1 vol %, more preferably at least 2, 4, 6, 8 or even at least 10 vol %. If the CO content is too high, conversion of $CO_2$ may be reduced, the CO content of the feed gas is therefore preferably at most 25 vol %, more preferably at most 22 vol %. Conventional $CO_2$ hydrogenation processes as described in the prior art are generally characterized in that the used feed gas mixture comprises no CO or only a very low concentration of CO.

In the process according to the invention the feed gas can have a temperature from ambient up to a maximum of about 350° C., before it is further heated in step (1) in the presence of a catalyst. In fact, it is the very essence of the present invention to not expose the feed gas to temperatures above 350° C. unless a catalyst is present as specified for step (1), in order to prevent coke formation (e.g. as a result of the Boudouard reaction). Preferably, the initial feed temperature is thus at most 325° C., or more preferably at most 300° C. to further suppress coke formation.

Typically, a syngas mixture after being obtained in a high temperature reforming step is cooled to ambient temperatures, in order to condense and separate water from the gas mixture. In the process according to the invention the feed gas mixture can, if desired, be pre-heated up to said maximum initial feed temperature by conventional means, e.g. via a heat exchanger.

In step (1) of the process according to the invention the feed gas mixture is heated in a first zone to a temperature within a reaction temperature range while in contact with a first catalyst. With reaction temperature range reference is made to the RWGS reaction that takes place in step (2).

The RWGS reaction can be performed, in the presence of a suitable catalyst, within a temperature range of about 450 to about 1000° C.; preferably at 500-800° C.; more preferably at 505-750° C.; and most preferably at 525-650° C.

A further characterizing aspect of the process of the present invention is that the heating of the feed gas to a temperature within the reaction temperature range occurs in a first zone. In a preferred way of operating the process according to the invention, the feed gas is heated to a temperature in step (1) that is the same or similar to that in step (2). In a further preferred way of operating the process according to the invention, the temperature in step (1) is higher than that in step (2), because the RWGS reaction is endothermic and heating in the first zone can be considered pre-heating the feed gas to a suitable reaction temperature, without the danger of coke formation. Preferably, the temperature in step (1) is about 50° C. higher than that in step (2).

In step (1) of the process according to the invention the feed gas mixture is heated in a first zone in the presence of a first catalyst. Suitable catalysts include all catalyst compositions known to be active in promoting the RWGS reaction, also referred to as RWGS catalyst. Suitable examples include several groups of metal oxides and composite (or mixed metal) oxides as listed in US2007/0142482 as RWGS catalysts, including compositions based on or containing ZnO, $MnO_x$, alkaline earth metal oxide, as catalytically active component, and supported on or co-precipitated with for example chromia, alumina, zirconia, magnesia, silica or mixtures thereof.

Preferably, a chromia/alumina catalyst composition, and more preferably a spent chromia/alumina dehydrogenation catalyst, that is a catalyst that has been used in an alkane dehydrogenation process, has undergone regeneration steps, and shows a significantly decreased dehydrogenation activity as defined in the co-pending application PCT/EP08/005069, is applied as the first catalyst in step (1). Without wishing to be bound to any theory, the inventors believe this catalyst actively prevents coke deposition by catalysing oxidation of any carbon formed with water into carbon monoxide and hydrogen; and also shows favourable activity as a RWGS catalyst.

Preferably, the chromia/alumina catalyst composition substantially consists of chromium (in the form of its oxides) as active constituent, optionally at least one alkali metal or alkaline earth metal as promoter, and alumina as support. The catalyst may further contain other inert components, like a binder material, or usual impurities as known to the skilled person.

In step (2) of the process according to the invention the heated feed gas is subsequently contacted in a second zone within the reaction temperature range with a second catalyst.

As indicated above, this RWGS reaction can be performed within a temperature range of about 450-1000° C., preferably at 500-800° C.; more preferably at 505-750° C.; and most preferably at 525-650° C. The temperature setting may the same as or different from step (1).

The RWGS reaction in step (2), as well as step (1), can be performed in a wide pressure range; for example from 0.1 to 10 MPa, but preferably at 0.1-2 MPa.

The second catalyst that is applied in step (2) can be any catalyst composition known to be active in promoting the RWGS reaction, also referred to as RWGS catalyst. Suitable examples include several groups of metal oxides and composite (or mixed metal) oxides as described in US2007/0142482 as RWGS catalysts, including compositions based on or containing ZnO, $MnO_x$, or alkaline earth metal oxides as catalytically active component(s), and supported on or co-precipitated with for example chromia, alumina, zirconia, magnesia, silica or mixtures thereof; and chromia/alumina as described in co-pending application PCT/EP08/005069. The second catalyst may be the same as or different from the first catalyst as used in step (1). In view of minimizing process complexity, the first and second catalysts are preferably the same, especially if the first and second zones are parts of one reactor.

Step (1) and step (2) of the process according to the invention can be performed in separate units or reactors. Preferably, use is made of equipment that allows continuous operation of the process. Step (1) basically is a pre-heating step, although the RWGS reaction may also proceed to some extent, and the equipment used may have been designed to optimise heat transfer.

In a preferred way of operating the process according to the invention both steps are performed in the same reactor, i.e. the first and second zones are subsequent zones of one reactor. The type of reactor is not specifically critical, and the skilled man can select a reactor that is suitable for the endothermic RWGS reaction, based on his general knowledge. Typically, a tubular reactor, or a multi-tubular reactor is applied, with at least one packed bed of catalyst.

Traditionally, a packed bed reactor has an entry zone with a gas distribution device, an empty space, and/or a bed of inert particles (like silica or quartz), which serve to properly distribute the incoming gas over the subsequent reaction zone and to pre-heat the gas. In the process according to the invention there should not be such an empty or inert particle bed pre-heating zone, because the feed gas should not be heated above 350° C. without a suitable catalyst being present. It is therefore preferred that a reactor completely filled with catalyst particles is used in the process according to the invention.

The invention further relates to use of the syngas mixture obtained with the process according to the invention as feed material for a process of making a further chemical product; like aliphatic oxygenates, especially methanol production, direct dimethyl ether synthesis, olefin synthesis (e.g. via Fischer-Tropsch reaction), aromatics production, carbonylation of methanol, carbonylation of olefins, or the reduction of iron oxide in steel production.

The invention therefore further relates to a process for making an organic chemical product using a syngas mixture as an intermediate or as feed material, which process comprises a step wherein carbon dioxide is reacted with hydrogen according to the invention. The term "organic chemical product" is very well known in the art and includes, but is not limited to, compounds containing C—H bonds. Examples of such a process are indicated above.

In a preferred embodiment, the invention concerns a process of making dimethyl ether directly from a syngas mixture having a $H_2/CO$ ratio of close to 1. For the step of making DME from syngas in this process, any suitable synthesis process as known in the art can be applied. Preferably, the slurry phase process as described in Proc. $8^{th}$ Natural gas Conversion Symp. 2007, Elsevier, ISBN 0444530789, p. 403 ff is applied.

In another preferred embodiment, the invention concerns a process of making methanol via synthesis gas, comprising steps (1) and (2) of the process according to the invention to result in a syngas mixture of suitable stoichiometry; i.e. preferably having a $H_2/CO$ ratio of about 2. For the step of making methanol from syngas in this process, any suitable synthesis process as known in the art can be applied.

The invention will now be further elucidated with the following experiments.

COMPARATIVE EXPERIMENT A

A quartz tubular reactor of 450 mm length and 12 mm diameter, with gas inlet on top and gas outlet at the bottom was placed vertically. The bottom part was filled with 8 ml of spent chromia/alumina catalyst (Catofin® from SudChemie (DE)). This second zone was about 70 mm in height, the remaining 50 mm above this catalyst bed was left empty, and is referred to as the first zone. The first zone was heated at 500° C., the second zone at 560° C. A feed gas of room temperature was fed to the first zone at a flow rate of 52 ml/min and at atmospheric pressure. The composition of the product gas stream was monitored hourly by in-line GC measurement, after quenching and removing water formed. In Table 1 feed gas and product gas composition (after 32 hours) are given. Carbon dioxide conversion was about 36%. It was noticed that the amount of methane in the product increased with time, and coke deposition was seen in the first zone after about one week.

COMPARATIVE EXPERIMENT B

CE A was repeated, but now the first zone was filled with quartz particles, and both zones were heated to 600° C. Results presented in Table 1 indicate similar conversion, and also increasing amount of methane with time as well as visible coke formation. After about 1 week the experiment was stopped: the first zone appeared to be virtually blocked by accumulated coke deposits.

COMPARATIVE EXPERIMENT C

In this experiment the reactor zones were completely filled with quartz particles, and were heated at 450 and 560° C., respectively. Passing the same feed gas as in CE A and B, some methane formation was observed, as well as coke formation in both zones. Only some carbon dioxide appeared to be converted into carbon monoxide.

EXAMPLE 1

Both reactor zones were now completely filled with chromia/alumina catalyst, experiments were further performed analogously to CE B. Results summarized in Table 1 indicate significantly higher carbon dioxide conversion (about 52%), whereas no methane was detected. Product gas composition was virtually stable over a period of 3 weeks, and no coke deposits were observed.

EXAMPLE 2

Example 1 was repeated, be it that the temperature of the second zone was now 560° C. (in stead of 600° C.). Slightly lower carbon dioxide conversion resulted (about 48%), the reaction ran stably during 3 weeks without methane or coke being observed.

These experiments show that with the process according to the invention the CO content of a $CO_2$, CO and $H_2$ gas mixture containing significant amounts of CO—over 20 vol % in the examples—can be increased (for example from $H_2/CO$ ratio of about 3 to about 1.6) in a stable process without occurrence of problems related to coke formation.

TABLE 1

| gas component | feed gas composition (vol %) | CE A (vol %) | CE B (vol %) | CE C (vol %) | Example 1 (vol %) | Example 2 (vol %) |
| --- | --- | --- | --- | --- | --- | --- |
| $H_2$ | 60.8 | 57.3 | 57.9 | 60.2 | 56.0 | 56.4 |
| $CO_2$ | 18.3 | 11.7 | 11.4 | 17.2 | 8.7 | 9.5 |
| CO | 20.8 | 30.6 | 30.5 | 22.4 | 35.1 | 34.0 |
| $CH_4$ | 0.0 | 0.2 | 0.2 | 0.1 | 0.0 | 0.0 |
| total | 99.9 | 99.8 | 100.0 | 99.9 | 99.8 | 99.9 |
| $H_2/CO$ | 2.9 | 1.9 | 1.9 | 2.7 | 1.6 | 1.7 |

The invention claimed is:

1. A process for making an organic chemical product, comprising:
   (1) heating a feed gas mixture having an initial feed temperature of at most 350 °C. in a first zone to a temperature within a reaction temperature range in the presence of a first catalyst, wherein the reaction temperature range is 505° C.-750° C.;
   (2) contacting the heated feed gas in a second zone within the reaction temperature range with a second catalyst; and
   making the organic chemical product, wherein the organic chemical product is methanol and/or dimethyl ether;
   wherein a syngas mixture is used as an intermediate in step (2) or as feed material in step (1).

2. The process of claim 1, wherein the CO content of the feed gas is at least 1 vol %.

3. The process of claim 1, wherein the temperature in step (1) is about 50° C. higher than that in step (2).

4. The process of claim 1, wherein the first catalyst in step (1) is a chromia/alumina catalyst.

5. The process of claim 1, wherein steps (1) and (2) are performed in the same reactor.

6. The process of claim 1, wherein the first and second catalysts are the same.

7. The process of claim 1, wherein the process is run continuously for at least three weeks.

8. The process of claim 1, wherein the reaction temperature range is 525-650 °C.

9. The process of claim 1, wherein the feed gas mixture comprises carbon dioxide, hydrogen, and carbon monoxide.

10. The process of claim 1, wherein the syngas mixture comprises carbon dioxide, hydrogen, and carbon monoxide.

11. The process of claim 1, wherein the feed gas mixture comprises the syngas mixture.

* * * * *